United States Patent
Ishii et al.

(10) Patent No.: US 11,109,829 B2
(45) Date of Patent: Sep. 7, 2021

(54) MEDICAL IMAGE DIAGNOSTIC APPARATUS

(71) Applicant: Toshiba Medical Systems Corporation, Otawara (JP)

(72) Inventors: Hideaki Ishii, Nasushiobara (JP); Satoshi Wakai, Nasushiobara (JP); Kazumasa Arakita, Nasushiobara (JP); Takuma Igarashi, Nasushiobara (JP); Yasuko Fujisawa, Nasushiobara (JP); Shigeo Kaminaga, Otawara (JP); Kenji Hirohata, Tokyo (JP); Junichiro Ooga, Tokyo (JP)

(73) Assignee: Canon Medical Systems Corporation, Otawara (JP)

( * ) Notice: Subject to any disclaimer, the term of this patent is extended or adjusted under 35 U.S.C. 154(b) by 753 days.

(21) Appl. No.: 14/329,441

(22) Filed: Jul. 11, 2014

(65) Prior Publication Data

US 2014/0323858 A1 Oct. 30, 2014

Related U.S. Application Data

(63) Continuation of application No. PCT/JP2013/082219, filed on Nov. 29, 2013.

(30) Foreign Application Priority Data

Nov. 30, 2012 (JP) .............................. JP2012-263417

(51) Int. Cl.
*A61B 6/00* (2006.01)
*A61B 6/03* (2006.01)

(52) U.S. Cl.
CPC ............... *A61B 6/504* (2013.01); *A61B 6/03* (2013.01); *A61B 6/032* (2013.01)

(58) Field of Classification Search
None
See application file for complete search history.

(56) References Cited

U.S. PATENT DOCUMENTS

| | | | | |
|---|---|---|---|---|
| 7,306,562 B1 * | 12/2007 | Baykal | ................... | G16H 50/20 600/481 |
| 2003/0208116 A1 * | 11/2003 | Liang | ..................... | A61B 5/055 600/407 |

(Continued)

FOREIGN PATENT DOCUMENTS

| CN | 102415898 A | 4/2012 |
|---|---|---|
| JP | 2009-82407 A | 4/2009 |

(Continued)

OTHER PUBLICATIONS

Rambhia et al., Jul. 2012, "Microcalcifications Increase Coronary Vulnerable Plaque Rusture Potential: A Patient-Based Micro-CT Fluid-Structure Interaction Study". Annals of Biomedical Engineering, vol. 40, No. 7, pp. 1443-1454.*

(Continued)

*Primary Examiner* — Yi-Shan Yang
(74) *Attorney, Agent, or Firm* — Oblon, McClelland, Maier & Neustadt, L.L.P.

(57) ABSTRACT

A medical image diagnostic apparatus according to an embodiment includes an estimation unit, an extraction unit, and a specifying unit. The estimation unit estimates a position of a plaque in a blood vessel based on data of CT images constituting a time series, with the blood vessel being enhanced by a contrast medium. The extraction unit extracts regions constituting the blood vessel from the CT images. The specifying unit specifies stress values respectively corresponding to the regions based on a moving displacement due to cardiac pulsation in each of the regions, and specifies an exfoliation risk of the plaque based on an (Continued)

index indicating hardness of the plaque and the stress value in the region corresponding to the position of the plaque.

8 Claims, 4 Drawing Sheets

(56) References Cited

U.S. PATENT DOCUMENTS

| | | | | |
|---|---|---|---|---|
| 2004/0255957 | A1* | 12/2004 | Cafferata | A61B 17/22 128/898 |
| 2006/0036167 | A1* | 2/2006 | Shina | A61B 6/12 600/433 |
| 2008/0101667 | A1* | 5/2008 | Begelman | A61B 5/02007 382/128 |
| 2009/0016483 | A1* | 1/2009 | Kawasaki | A61B 5/02007 378/4 |
| 2010/0017182 | A1* | 1/2010 | Voros | G16B 20/00 703/11 |
| 2012/0041318 | A1* | 2/2012 | Taylor | A61B 5/02007 600/504 |
| 2012/0063663 | A1 | 3/2012 | Kawasaki | |
| 2012/0243764 | A1* | 9/2012 | Dey | A61B 6/032 382/131 |
| 2013/0083985 | A1* | 4/2013 | Wiets | A61B 6/487 382/130 |
| 2015/0148679 | A1* | 5/2015 | Thiele | A61B 8/065 600/454 |

FOREIGN PATENT DOCUMENTS

| | | |
|---|---|---|
| JP | 2012-81254 A | 4/2012 |
| JP | 2014-61268 A | 4/2014 |
| JP | 2014-108198 A | 6/2014 |
| JP | 2014-108208 A | 6/2014 |
| JP | 2014-113264 A | 6/2014 |
| JP | 2014-128650 A | 7/2014 |
| JP | 2014-128651 A | 7/2014 |
| WO | WO 2012/021307 A2 | 2/2012 |

OTHER PUBLICATIONS

Komatus et al., 2005, "Deletion of Coronary PLaque by Computed Tomography With a Novel plaque Analysis System, "Plaque Map", and COmparison with Intravascular Ultrasound and Angioscopy". Circ. J. 2005; 69:72-77.*

Kim et al., 2010, "Patient-Specific Modeling of Blood Flow and Pressure in Human Coronary Arteries" October, Annals of Biomedical Engineering, vol. 38, No. 10, pp. 3195-3209.*

Salvucci et al. 2010, "A patient-specific method for the evaluation of wall shear stress in human coronary arteries" 32nd Annual International Conference of the IEEE EMBS. pp. 3788-3791.*

Fornell, Jul. 3, 2012, the Latest Advances in Coronary CT Angiography Software.*

Jim Version 3.0. www.xinapse.com. 2005.*

Obaid et al., "Atherosclerotic plaque composition and classification identified by coronary computed tomography". Circ Cardopvasc Imaging, 2013;6:655-664. (Year: 2013).*

Combined Office Action and Search Report dated Sep. 25, 2015 in Chinese Patent Application No. 201380003267.X (with English Translation of Category of Cited Documents).

"Chinese Master Theses Full-Text Database" Medicine and Health Sciences, Dec. 31, 2009, 10 Pages (with English language translation).

International Search Report dated Jan. 21, 2014 for PCT/JP2013/082219 filed Nov. 29, 2013 with English Translation.

International Written Opinion dated Jan. 21, 2014 for PCT/JP2013/082219 filed Nov. 29, 2013.

Salvucci, F.P., Perazzo, C.A., Gurfinkel, E., Armentano, R.L., Barra, J.G., A patient-specific method for the evaluation of wall shear stress in human coronary arteries, Engineering in Medicine and Biology Society (EMBC), 2010 Annual International Conference of the IEEE, Aug. 31, 2010, pp. 3788-3791.

Taewon Seo, Seok Hyeon Jeong, Dong Ha Kim, Dongjin Seo, The blood flow simulations of human aortic arch model with major branches, Biomedical Engineering and Informatics (BMEI), 2011 4th International Conference on Oct. 15, 2011, vol. 2, pp. 923-926.

Li-Na Pu, Ping Yang, Xin-Yu Zhang, Yuan-Ting Zhang, A quantitative study of the effect of blood viscosity and bulk modulus of plaque compositions on the vulnerability of an atherosclerotic plaque using a 3D fluid-structure interaction model, Biomedical and Health Informatics (BHI), 2012 IEEE—EMBS International Conference on, Jan. 5, 2012, pp. 245-248.

Office Action dated Dec. 20, 2016 in Japanese Patent Application No. 2016-185339.

* cited by examiner

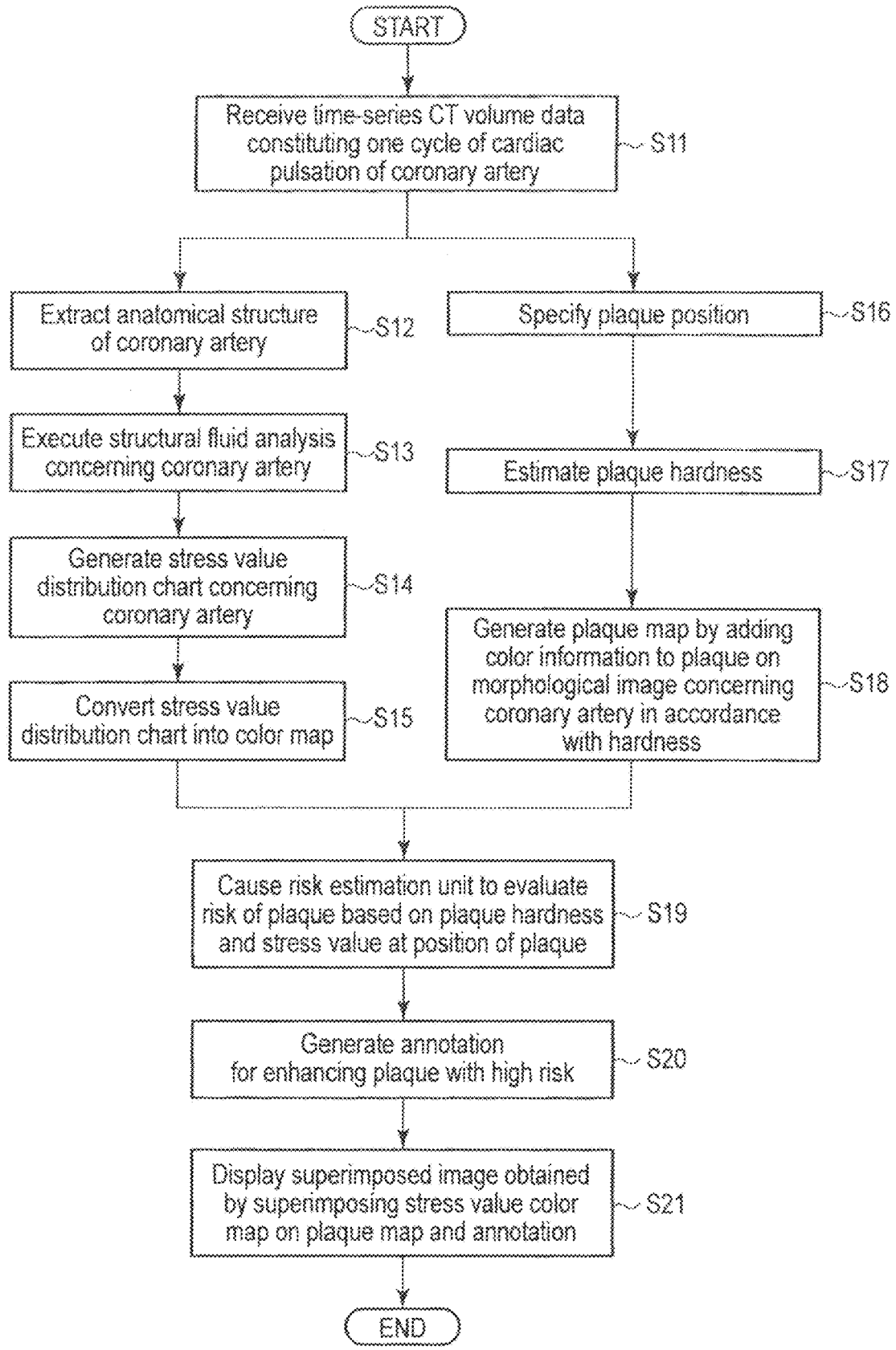
F I G. 2

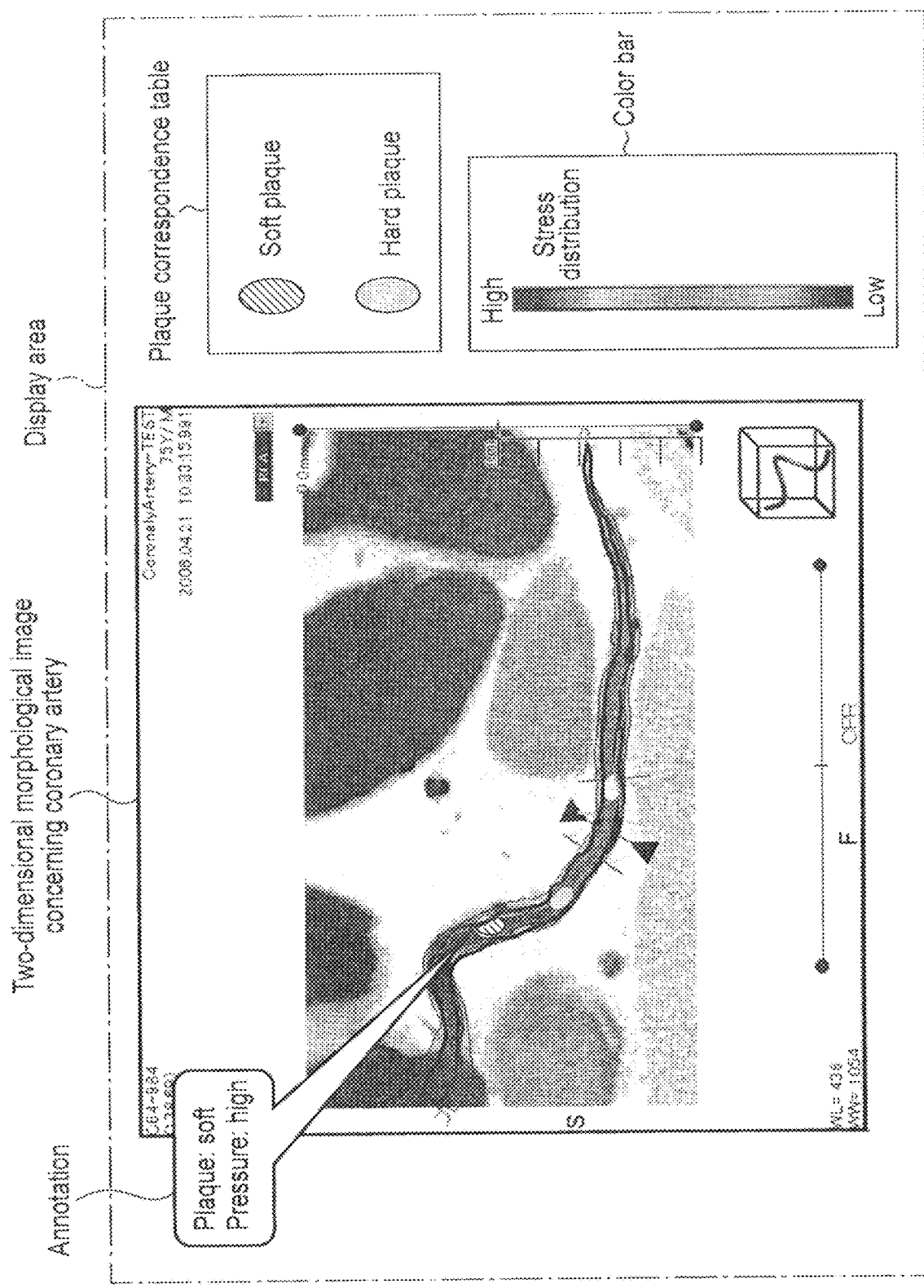
F I G. 4

MEDICAL IMAGE DIAGNOSTIC APPARATUS

CROSS-REFERENCE TO RELATED APPLICATIONS

This application is a Continuation application of PCT Application NO. PCT/JP2013/082219, filed Nov. 29, 2013 and based upon and claims the benefit of priority from the Japanese Patent Application NO. 2012-263417, filed Nov. 30, 2012, the entire contents of all of which are incorporated herein by reference

FIELD

Embodiments described herein relate generally to a medical image diagnostic apparatus.

BACKGROUND

The number of fatalities caused by so-called thrombotic diseases such as cerebral infarction and myocardial infarction is still large. Plaque exfoliation is one of the causes of myocardial infarction. Plaque is formed when substances such as cholesterol fat and macrophages in blood are deposited on the intima of a coronary artery. If plaque peels due to inner pressure or the like, a thrombosis is formed at the peeling portion. The thrombosis then flows on the blood flow and clogs the coronary artery, thereby causing myocardial infarction. In order to prevent myocardial infarction, therefore, it is necessary to remove plaque which is likely to peel by percutaneous coronary intervention or the like. Determination on whether to require percutaneous coronary intervention uses, for example, a measurement result of FFR (Functional Flow Reserve) using a pressure wire. However, it is necessary for FFR measurement to insert a pressure wire into a patient. This imposes a heavy burden on the patient. Demands have therefore arisen for a method of determining the necessity of percutaneous coronary intervention without imposing much burden on patients.

There is currently available a technique of estimating plaque characteristics based on the CT values of a CT image captured by a CT (Computed Tomography) apparatus for the purpose of reducing burden on a patient. It is however difficult to determine whether a given plaque is a plaque with a high risk which is likely to peel.

BRIEF DESCRIPTION OF THE DRAWINGS

FIG. 2 is a flowchart for explaining plaque-enhanced display processing performed by the medical image diagnostic apparatus according to this embodiment.

FIG. 4 is a view showing an example of the two-dimensional superimposed image displayed on the display unit by the plaque-enhanced display function of the medical image diagnostic apparatus according to this embodiment.

DETAILED DESCRIPTION

Figure 1:
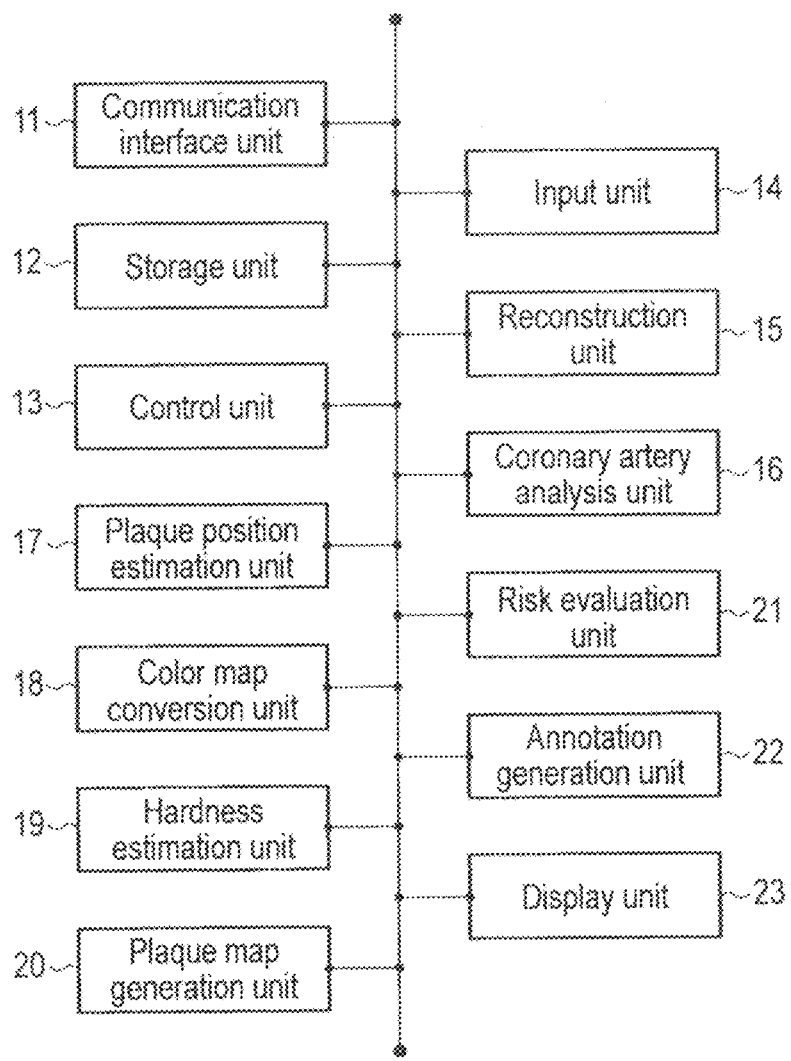
FIG. 1 is a block diagram showing an example of the arrangement of a medical image diagnostic apparatus according to an embodiment.

A medical image diagnostic apparatus according to an embodiment includes an estimation unit, an extraction unit, and a specifying unit. The estimation unit estimates a position of a plaque in a blood vessel based on data of a plurality of CT images constituting a time series, with the blood vessel being enhanced by a contrast medium. The extraction unit extracts a plurality of regions constituting the blood vessel from the CT images. The specifying unit specifies a plurality of stress values respectively corresponding to the plurality of regions constituting the blood vessel based on a moving displacement due to cardiac pulsation in each of the regions constituting the blood vessel, and specifies an exfoliation risk of the plaque based on an index indicating hardness of the plaque and the stress value in the region corresponding to the position of the plaque.

A medical image diagnostic apparatus 1 according to this embodiment will be described below with reference to the accompanying drawings. Note that the same reference numerals denote constituent elements having almost the same functions and arrangements in the following description, and a repetitive description will be made only when required.

FIG. 1 is a block diagram showing an example of the arrangement of the medical image diagnostic apparatus 1 according to this embodiment. As shown in FIG. 1, the medical image diagnostic apparatus 1 includes a communication interface unit 11, a storage unit 12, a control unit 13, an input unit 14, a reconstruction unit 15, a coronary artery analysis unit 16 (extraction unit 16), a plaque position estimation unit 17, a color map conversion unit 18, a hardness estimation unit 19, a plaque map generation unit 20, a risk evaluation unit 21 (specifying unit 21), an annotation generation unit 22, and a display unit 23.

The medical image diagnostic apparatus 1 according to this embodiment is connected to external apparatuses such as a CT apparatus, SPECT apparatus, PET apparatus, and PACS (Picture Archiving and Communication System) via a network such as a LAN (Local Area Network) or public electronic communication line.

The medical image diagnostic apparatus 1 includes the communication interface unit 11 for connection to an external apparatus via a network. The communication interface unit 11 includes, for example, a connector unit (not shown) for connection to an external apparatus or the like via a wired cable and a wireless signal reception unit (not shown) for receiving a wireless signal from the external apparatus. The medical image diagnostic apparatus 1 transmits and receives data to and from an external apparatus via the communication interface unit 11 under the control of the control unit 13 (to be described later).

The storage unit 12 includes a semiconductor storage device such as a flash SSD (Solid State Disk) as a semiconductor storage element and an HDD (Hard Disk Drive). The storage unit 12 stores the data of an image to be processed by the medical image diagnostic apparatus 1, which is transmitted from an external apparatus, under the control of the control unit 13. The data of the image to be processed is the data of a series of images continuously and repeatedly captured throughout one cycle of cardiac pulsation while a coronary artery is contrast-enhanced with a tracer. The data of a series of images is typically time-series CT volume data constituting one cycle of cardiac pulsation acquired by the CT apparatus. Note that the storage unit 12 may keep holding the above image data received via the communication interface unit 11 and stored or may erase the data in response to the end of the operation of the medical image diagnostic apparatus 1 by the user. That is, in the medical image diagnostic apparatus 1, the storage unit 12 may only function as a memory which temporarily stores the above image data received via the communication interface unit 11.

In addition, the storage unit 12 stores data concerning a CT value correspondence table in which the data of a plurality of CT values are associated with the data of indices indicating the hardnesses of a plurality of plaques. An index indicating the hardness of a plaque is, for example, the hardness (hardness degree) of the plaque. For the sake of simplicity, an index indicating the hardness of a plaque will be referred to as a plaque hardness.

In addition, the storage unit 12 stores data concerning a risk correspondence table in which the data of a plurality of stress values and the data of a plurality of plaque hardnesses are associated with the data of a plurality of exfoliation risks. Note that a risk table may be provided for each object information, each region, or each narrow region range. Object information includes, for example, the age, weight, and sex of an object. Each region includes the heart and the brain.

The control unit 13 includes a CPU (Central Processing Unit) and a memory circuit. The control unit 13 receives the information input from the input unit 14 and temporarily stores it in the memory circuit. The control unit 13 controls each unit of the medical image diagnostic apparatus 1 based on the input information. In addition, the control unit 13 comprehensively controls write processing of the data generated or received from each unit into the storage unit 12 and readout processing of data from the storage unit 12 to each unit.

The input unit 14 functions as an interface for accepting the instruction information issued by the user with respect to the medical image diagnostic apparatus 1. As the input unit 14, it is possible to properly use an input device such as a mouse, keyboard, trackball, touch panel, or button. More specifically, the input unit 14 accepts an input of a tomographic image of the coronary artery which is desired by the user. The input unit 14 accepts the desired coronary artery image in accordance with a user operation on a three-dimensional CT image concerning the coronary artery displayed on the display unit 23 (to be described later).

The reconstruction unit 15 reconstructs a three-dimensional or two-dimensional CT image concerning the coronary artery based on CT (Computed Tomography) volume data. A three-dimensional or two-dimensional CT image concerning the coronary artery will be simply referred to as a CT image concerning the coronary artery.

The coronary artery analysis unit 16 calculates a plurality of stress values corresponding to a plurality of regions constituting the coronary artery based on the temporal change amount of the coronary artery due to the cardiac pulsation specified from time-series CT volume data constituting one cycle of cardiac pulsation. Note that the coronary artery analysis unit 16 may calculate a change in stress value or a stress value difference instead of a stress value in each region of the coronary artery. A change in stress value indicates a change in stress value concerning the same region in adjacent phases. In addition, a stress value difference indicates a stress value difference relative to a predetermined threshold, a difference from a stress value corresponding to the region designated by the user on the superimposed image displayed on the display unit 23, or the like. The coronary artery analysis unit 16 then generates a stress value distribution chart corresponding to a CT image. The coronary artery analysis unit 16 will be described in detail later.

The plaque position estimation unit 17 estimates a plaque position on a CT image concerning the coronary artery. The plaque position estimation unit 17 uses a change in the inner diameter of the coronary artery to estimate a plaque position. The inner diameter is defined by a length perpendicular to a coronary artery centerline in the coronary artery. The plaque position estimation unit 17 calculates the sizes of inner diameters at a plurality of points on the coronary artery. The plaque position estimation unit 17 estimates, as a plaque position, a position on the coronary artery at which the size of the inner diameter quickly decreases.

The color map conversion unit 18 converts the stress value distribution chart generated by the coronary artery analysis unit 16 into a stress value color map based on an LUT (Look Up Table) concerning stress values stored in advance in the storage unit 12. A stress value LUT is a correspondence table in which a plurality of pieces of color information is assigned to data concerning a plurality of stress values.

The hardness estimation unit 19 estimates the hardness of a plaque based on a CT value at the plaque position estimated by the plaque position estimation unit 17. More specifically, the hardness estimation unit 19 reads out data from the CT value correspondence table stored in the storage unit 12. The hardness estimation unit 19 then refers to the CT value correspondence table to estimate the hardness of the target plaque by comparing the CT value of the target plaque with a plurality of CT values in the CT correspondence table.

The plaque map generation unit 20 generates a plaque map by adding color information corresponding to a plaque hardness to a mark indicating a plaque on a CT image concerning the coronary artery. Color information is only required to be identified in accordance with a plaque hardness, and includes, for example, a color type and a color density. In addition, the plaque map generation unit 20 may change the shape of a mark indicating a plaque in accordance with a plaque hardness.

The risk evaluation unit 21 evaluates the risk of a plaque based on a plaque hardness and a stress value. More specifically, the risk evaluation unit 21 reads out the data of the risk correspondence table stored in the storage unit 12. The risk evaluation unit 21 then refers to the risk correspondence table to specify the exfoliation risk of the target plaque based on a stress value in a region corresponding to the position of the target plaque and the hardness of the target plaque. In this case, a hardness may be, for example, a numerical value or degree. Note that the risk evaluation unit 21 calculates a risk value based on a plaque hardness and a stress value. The risk evaluation unit 21 obtains a risk value by, for example, multiplying a value indicating a plaque hardness by a stress value in a region corresponding to the position of the plaque. The risk evaluation unit 21 then evaluates the risk of the plaque in accordance with the calculated risk value. For example, when risks are expressed by three stages, namely "risk: none", "risk: low", and "risk: high", the ranges of risks to be evaluated in the respective stages are assigned to the respective stages. The risk evaluation unit 21 then evaluates a risk in accordance with the calculated risk and the ranges of risks assigned to the respective stages. Note that the risk evaluation unit 21 may calculate a risk value by multiplying a CT value corresponding to the position of the target plaque by a stress value in a region corresponding to the position of the target plaque. Note that it is possible to change risk settings as needed in accordance with a user instruction.

The annotation generation unit 22 generates an annotation for enhancing a plaque with a high risk. Annotations include, for example, text information concerning the risk evaluation result on a plaque and graphic information corresponding to the risk evaluation result on the plaque. Text information may be, for example, information for notifying the user of an exfoliation risk such as "there is no risk" or "the risk is high" or information notifying the user of the necessity/unnecessity of a medical treatment, e.g., "no medical treatment is necessary" or "a medical treatment is required". At this time, the annotation generation unit 22 decides the necessity/unnecessity of a medical treatment in accordance with the exfoliation risk. Graphic information is, for example, a mark including a flag, circle, rectangle, or star.

The display unit 23 displays the superimposed image obtained by superimposing a plaque map and a press value color map on a CT image. In addition, the display unit 23 superimposes and displays the annotation generated by the annotation generation unit 22 on the above superimposed image so as to indicate the target plaque position on the image. Note that "so as to indicate the target plaque position" is to, for example, cause the display unit 23 to display an annotation such that the position on the image which is indicated by the annotation corresponds to the position of the plaque. Note that the display unit 23 displays a CT image, plaque map, stress value color map, and superimposed image in accordance with the instruction issued by the user via the input unit 14.

(Plaque-Enhanced Display Function)

The plaque-enhanced display function is a function by which the display unit 23 of the medical image diagnostic apparatus 1 according to this embodiment displays a plaque with a high risk in an enhanced state on the superimposed image obtained by superimposing a plaque map and a stress value map on a CT image. Processing based on the plaque-enhanced display function (to be referred to as plaque-enhanced display processing hereinafter) will be described below with reference to FIG. 2.

FIG. 2 is a flowchart for explaining plaque-enhanced display processing performed by the medical image diagnostic apparatus 1 according to this embodiment. First of all, the apparatus receives time-series CT volume data constituting one cycle of cardiac pulsation of the coronary artery from an external apparatus via the communication interface unit 11 (step S11). The storage unit 12 stores the received CT volume data.

The coronary artery analysis unit 16 extracts information concerning coronary artery centerlines and the anatomical structure of the coronary artery such as the inner wall of a blood vessel based on the CT value data (step S12). The coronary artery analysis unit 16 executes structural fluid analysis concerning stress values in a plurality of regions constituting the coronary artery based on the extracted anatomical structure of the coronary artery and physical parameters such as the viscosity value of blood flowing in the coronary artery (step S13). The coronary artery analysis unit 16 then generates a stress value distribution chart (step S14). The color map conversion unit 18 converts the stress value distribution chart into a stress value color map (step S15).

The plaque position estimation unit 17 estimates the position of a plaque on the CT image concerning the coronary artery based on the volume data (step S16). The hardness estimation unit 19 estimates the hardness of the plaque based on the CT value at the position of the plaque estimated by the plaque position estimation unit 17 (step S17). The plaque map generation unit 20 then generates a plaque map by adding color information corresponding to the hardness of the plaque to a mark indicating the plaque on the CT image concerning the coronary artery (step S18).

The risk evaluation unit evaluates the exfoliation risk of the plaque based on the hardness of the plaque and the stress value (step S19). If the evaluation result indicates that a plaque with a high risk exists on the CT image, the annotation generation unit 22 generates an annotation for enhancing the plaque with a high risk (step S20). The display unit 23 then displays the superimposed image obtained by superimposing a plaque map and a stress value color map and the annotation on the CT image (step S21).

An example of the superimposed image and the annotation displayed on the display unit 23 in step S20 will be described with reference to FIGS. 3 and 4.

Figure 3:
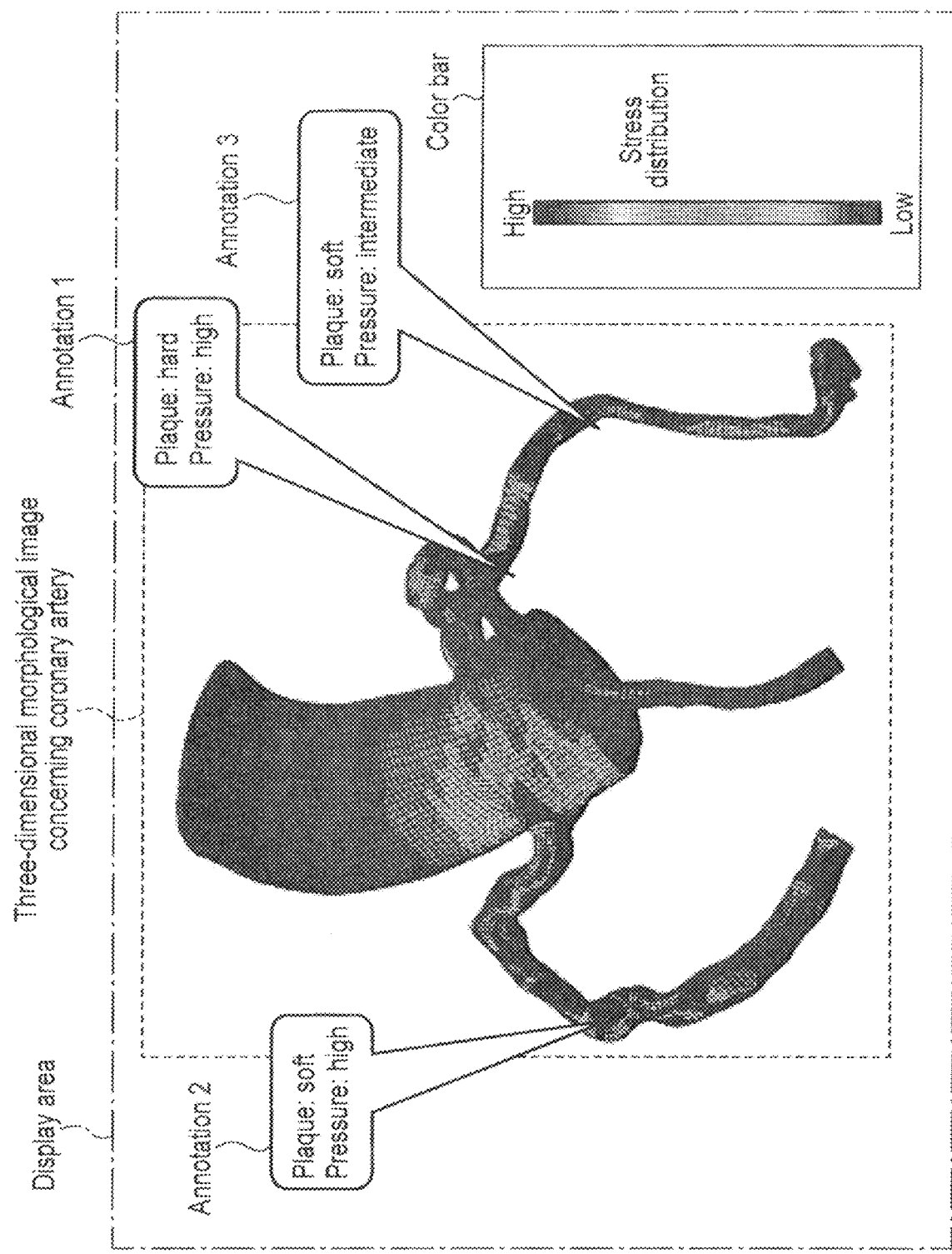
FIG. 3 is a view showing an example of the three-dimensional superimposed image displayed on a display unit by the plaque-enhanced display function of the medical image diagnostic apparatus according to this embodiment.

FIG. 3 is a view showing an example of a three-dimensional superimposed image displayed on the display unit 23 by the plaque-enhanced display function of the medical image diagnostic apparatus 1 according to this embodiment. FIG. 3 shows the superimposed image obtained by superimposing a three-dimensional plaque map and a stress value color map, a color bar, and a plurality of annotations on a three-dimensional CT image concerning the coronary artery. It is possible to switch between a CT image, superimposed image, plaque map, and stress value color map, as needed, in accordance with the instruction issued by the user via the input unit 14. The apparatus may display an icon for switching between these images on the display area. The color bar is an LUT used by the color map conversion unit 18 to convert the stress value distribution chart into the stress value color map. As shown in FIG. 3, the three blood vessel regions are enhanced by annotations. This indicates that the risk evaluation unit 21 determines that the risks of the plaques included in the three blood vessel regions are high. An annotation includes text information concerning a plaque characteristic (hardness) and a stress value. For example, annotation 1 indicates that the plaque is hard, and the stress value applied to the plaque is large. In addition, annotation 3 indicates that the plaque is soft, and the stress value is intermediate. It is possible to change a determination criterion for an exfoliation risk, as needed, which is used by the risk evaluation unit 21 in accordance with a user instruction.

FIG. 4 is a view showing an example of the two-dimensional superimposed image displayed on the display unit 23 by the plaque-enhanced display function of the medical image diagnostic apparatus 1 according to this embodiment. FIG. 4 shows the superimposed image obtained by superimposing a plaque map and a stress value color map on a CT image concerning the coronary artery, a color bar, annotations, and a plaque correspondence table.

A stress value color map is only required to indicate stress values applied to a blood vessel wall. For example, as shown in FIG. 4, the stress value color map is displayed while being positionally matched with the CT image. As a result, marks indicating the magnitudes of stress values are displayed on a blood vessel wall along a blood vessel contour. A plaque correspondence table serves to notify the user of the hardnesses of plaques, and displays, for example, colors corresponding to the hardnesses of the plaques, as shown in FIG. 4. In addition, although FIG. 4 shows the hardnesses of the plaques in two stages, it is possible to display the hardnesses in three or more stages. A color bar is displayed based on an LUT used by the color map conversion unit 18 to convert a stress value distribution chart into a stress value color map, and expresses the magnitudes of stress values in color. In addition, an annotation indicates the position of a plaque and includes text information for notifying the user of the characteristics of the plaque and a stress value applied to the position of the plaque. This notification is only required to notify the exfoliation risk of a plaque, and hence text information may be text information directly indicating an exfoliation risk, e.g., "exfoliation risk: high". If the exfoliation risks of a plurality of plaques are high, text information may include information indicating the order of exfoliation risks or the priority order of medical treatment of the plurality of plaques.

Note that it is possible to switch between the three-dimensional superimposed image and the two-dimensional superimposed image respectively shown in FIGS. 3 and 4 in accordance with the instruction issued by the user via the input unit 14. The method of displaying a stress value color map, the method of displaying plaque positions, the method of displaying plaque characteristics, and the method of displaying annotations shown in FIGS. 3 and 4 are examples. However, the display methods to be used are not limited to those described above as long as they enable the user to display the superimposed image obtained by superimposing a stress value color map and a plaque map and display a plaque with a high risk.

According to the plaque-enhanced display function described above, the following effects can be obtained.

The medical image diagnostic apparatus 1 according to this embodiment having the plaque-enhanced display function can generate a plaque map and a stress value color map based on time-series CT volume data constituting one cycle of cardiac pulsation of the coronary artery which are acquired by a CT apparatus or the like. The apparatus can display the superimposed image obtained by superimposing a stress value color map on a plaque map. The apparatus then can display a plaque with a high risk in an enhanced state on a superimposed image or the like. The risk evaluation unit 21 can automatically determine a risk based on the hardness of a plaque, a stress value applied to a blood vessel on which the plaque is located, and the like. It is therefore possible to estimate the risk of the plaque in consideration of the stress value applied to the plaque as well as the characteristics of the plaque.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. For example, as shown in FIG. 1, the medical image diagnostic apparatus 1 of this embodiment includes the storage unit 12 as a constituent element as described above. However, the data of images to be processed may be stored in other modalities, a PACS, and the like which are connected to the medical image diagnostic apparatus 1 via the communication interface unit 11. The storage unit 12 of the medical image diagnostic apparatus 1 may function as a memory for temporarily storing the data of an image to be processed. The accompanying claims and their equivalents are intended to cover such forms or modifications as would fall within the scope and spirit of the inventions.

The invention claimed is:

1. A medical image diagnostic apparatus comprising:
processing circuitry that
estimates a position of a plaque in a blood vessel based on data of a plurality of CT images constituting a time series, with the blood vessel being enhanced by a contrast medium,
estimates hardness of the plaque based on a CT value at the position, extracts a plurality of regions constituting the blood vessel from the plurality of CT images,
specifies a plurality of stress values respectively corresponding to the plurality of regions constituting the blood vessel based on a moving displacement due to cardiac pulsation in each of the regions constituting the blood vessel,
specifies an exfoliation risk of the plaque based on the estimated hardness and a stress value, of the plurality of stress values, in a region corresponding to the position, and
generates a color map of the stress values along a blood vessel contour of the blood vessel included in a CT image of the plurality of CT images by generating a stress value distribution chart and converting the stress value distribution chart into the color map; and
a display that
displays the CT image of the plurality of CT images,
displays a mark indicating (i) a position of a first plaque such that the mark is superimposed on the CT image and (ii) a priority order of a medical treatment of the first plaque or whether the medical treatment is necessary based on the specified exfoliation risk of the first plaque,
displays display information indicating a degree of the estimated hardness of the first plaque for the mark, and
displays the generated color map of the stress values along the blood vessel contour included in the CT image superimposed on the mark indicating the first plaque, wherein
the displayed CT image is a two-dimensional long-axis sectional image of the blood vessel, and
the display superimposes the mark and the generated color map on the two-dimensional long-axis sectional image.

2. The medical image diagnostic apparatus according to claim 1, wherein the display information is a color or pattern of the mark that indicates the degree of the hardness corresponding to the first plaque.

3. The medical image diagnostic apparatus according to claim 1, wherein the display displays the mark in color or shape corresponding to the first plaque.

4. The medical image diagnostic apparatus according to claim 1, wherein the display displays a text indicating the degree of the hardness corresponding to the first plaque.

5. The medical image diagnostic apparatus according to claim 1, wherein the display displays a text indicating a degree of the stress value in the region corresponding to the position of the first plaque.

6. The medical image diagnostic apparatus according to claim 1, wherein
the display displays an icon for switching a display mode, and
the processing circuitry, in response to an input via the icon, switches the display mode between displaying the CT image, the mark, and the generated color map.

7. The medical image diagnostic apparatus according to claim 1, wherein the display displays the CT image, the mark, the display information indicating the degree of the hardness, the generated color map of the stress value along the blood vessel contour, a color bar, and an annotation indicating the degree of the stress value and a degree of pressure.

8. A medical image diagnostic method comprising:
estimating, by processing circuitry, a position of a plaque in a blood vessel based on data of a plurality of CT images constituting a time series, with the blood vessel being enhanced by a contrast medium;
estimating, by the processing circuitry, hardness of the plaque based on a CT value at the position;
extracting, by the processing circuitry, a plurality of regions constituting the blood vessel from the plurality of CT images;
specifying, by the processing circuitry, a plurality of stress values respectively corresponding to the plurality of regions constituting the blood vessel based on a moving displacement due to cardiac pulsation in each of the regions constituting the blood vessel;
specifying, by the processing circuitry, an exfoliation risk of the plaque based on the estimated hardness and a stress value, of the plurality of stress values, in a region corresponding to the position;
generating, by the processing circuitry, a color map of the stress values along a blood vessel contour of the blood vessel included in a CT image of the plurality of CT images by generating a stress value distribution chart and converting the stress value distribution chart into the color map; and
displaying, on a display,
the CT image of the plurality of CT images,
a mark indicating (i) a position of a first plaque such that the mark is superimposed on the CT image and (ii) a priority order of a medical treatment of the first plaque or whether the medical treatment is necessary based on the specified exfoliation risk of the first plaque,
display information indicating a degree of the estimated hardness of the first plaque for the mark, and
the generated color map of the stress values along the blood vessel contour included in the CT image superimposed on the mark indicating the first plaque, wherein
the displayed CT image is a two-dimensional long-axis sectional image of the blood vessel, and
the displaying superimposes the mark and the generated color map on the two-dimensional long-axis sectional image.

* * * * *